(12) United States Patent  (10) Patent No.: US 8,074,693 B2
Yamamoto et al.  (45) Date of Patent: Dec. 13, 2011

(54) PROCESSING APPARATUS

(75) Inventors: Hiroki Yamamoto, Kagawa (JP); Kenji Takeuchi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 188 days.

(21) Appl. No.: 12/532,617

(22) PCT Filed: Apr. 3, 2008

(86) PCT No.: PCT/JP2008/056658
§ 371 (c)(1),
(2), (4) Date: Dec. 11, 2009

(87) PCT Pub. No.: WO2008/126748

PCT Pub. Date: Oct. 23, 2008

(65) Prior Publication Data
US 2010/0108268 A1   May 6, 2010

(30) Foreign Application Priority Data

Apr. 6, 2007  (JP) ................................ 2007-100991

(51) Int. Cl.
*B32B 37/00* (2006.01)
(52) U.S. Cl. ..................... 156/510; 156/73.1; 156/580.1; 156/580.2
(58) Field of Classification Search ................. 156/73.1, 156/73.3, 510, 515, 530, 555, 580.1, 580.2, 156/582
See application file for complete search history.

(56) References Cited

U.S. PATENT DOCUMENTS

| 4,479,836 | A | * | 10/1984 | Dickover et al. ............... 156/164 |
| 4,713,132 | A | * | 12/1987 | Abel et al. ..................... 156/73.1 |
| 7,383,865 | B2 | * | 6/2008 | Umebayashi et al. ......... 156/350 |
| 7,449,084 | B2 | * | 11/2008 | Nakakado .................. 156/580.1 |
| 2004/0035521 | A1 | | 2/2004 | Nakakado et al. |
| 2004/0112508 | A1 | | 6/2004 | Umebayashi et al. |
| 2005/0241751 | A1 | | 11/2005 | Nakakado et al. |
| 2006/0032589 | A1 | | 2/2006 | Nakakado et al. |
| 2006/0089615 | A1 | | 4/2006 | Saito |

FOREIGN PATENT DOCUMENTS

EP         1 393 701 A2    3/2004
(Continued)

OTHER PUBLICATIONS

PCT/JP2008/056658 International Search Report.

*Primary Examiner* — James Sells
(74) *Attorney, Agent, or Firm* — Lowe, Hauptman, Ham & Berner, LLP

(57) ABSTRACT

A processing apparatus that performs processing on a workpiece continuous in a transport direction, and performs processing on the workpiece at a predetermined processing pitch in a rotational direction of a rotating body that rotates about an axis, includes: a first processing section that is disposed at a predetermined position in the rotational direction so as to oppose an outer circumferential face of the rotating body, second processing sections at each predetermined angle in the rotational direction on the outer circumferential face of the rotating body, which perform the processing on the workpiece in cooperation with the first processing section when a second processing section opposes the first processing section, and a support section that supports the workpiece between the second processing sections, and in which it is possible to change, depending on the processing pitch, a position at which the support section supports the workpiece.

8 Claims, 14 Drawing Sheets

FOREIGN PATENT DOCUMENTS

| | | |
|---|---|---|
| EP | 1 428 487 A1 | 6/2004 |
| EP | 1 795 164 A1 | 6/2007 |
| JP | 2004-223238 A | 8/2004 |
| JP | 2004-329873 A | 11/2004 |
| JP | 2006-101970 A | 4/2006 |
| JP | 2006-326313 A | 12/2006 |
| JP | 2007-044374 A | 2/2007 |

* cited by examiner

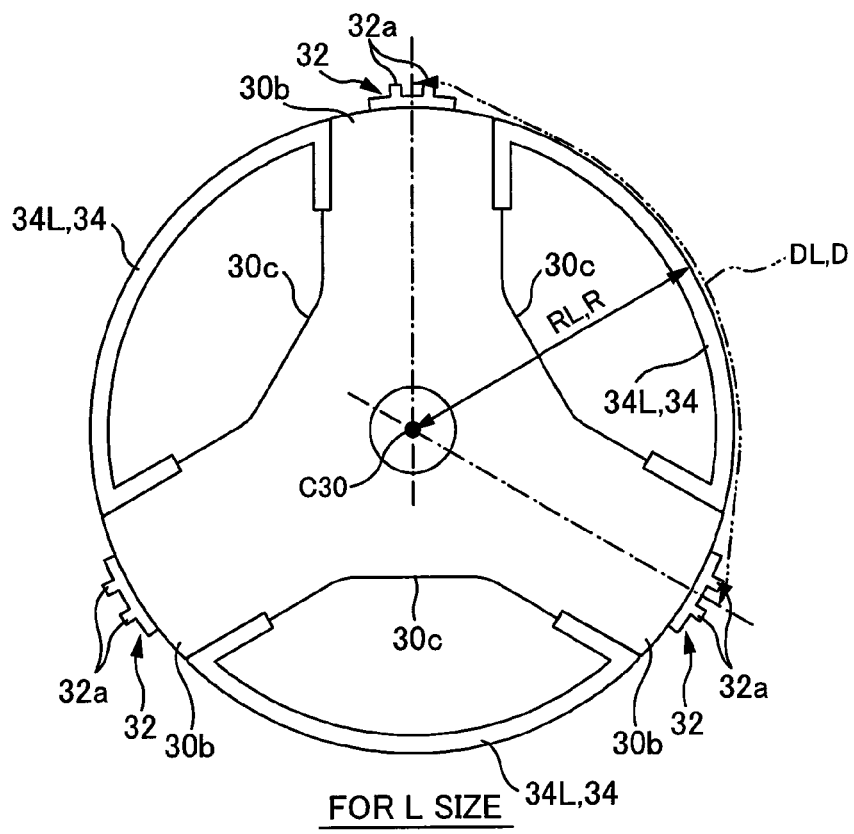
FIG. 4A  FOR L SIZE
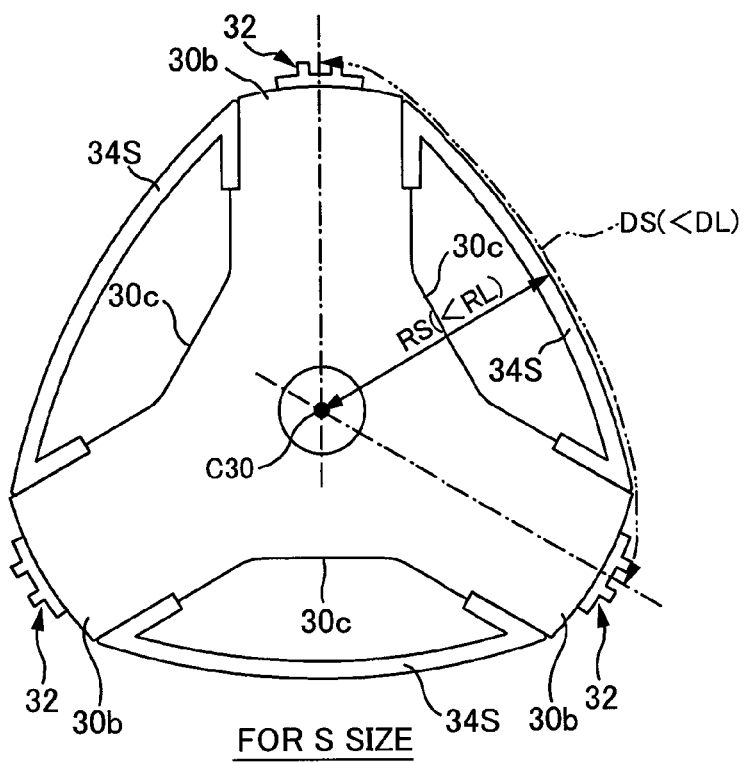
FIG. 4B  FOR S SIZE

PROCESSING APPARATUS

RELATED APPLICATIONS

The present application is based on International Application PCT/JP2008/056658, filed Apr. 3, 2008, which claims priority from Japan Application Number 2007-100991, filed Apr. 6, 2007, the disclosures of which are hereby incorporated by reference herein in their entirety.

TECHNICAL FIELD

The present invention relates to a processing apparatus that is used to produce products such as disposable diapers and that performs processing on a continuous workpiece at a predetermined processing pitch before the continuous workpiece is severed into product units.

BACKGROUND ART

Conventionally, disposable diapers (hereinafter referred to as "diapers") have been produced in a continuous production line. One of processes for producing disposable diapers involves a process in which a plurality of continuous sheets are superposed and an welding process is performed on those sheets in a direction of continuation at a processing pitch of a product unit, thereby joining the plurality of sheets. This process is performed using a so-called sealing apparatus (for example, see JP-A-2006-101970).

DISCLOSURE OF INVENTION

Problem to be Solved by the Invention

A sealing apparatus includes a drum that is driven and rotates about an axis, and an ultrasonic horn that is disposed in a predetermined position in a rotational direction of the drum and that opposes an outer circumferential face of the drum. Also, anvils that respectively include a projection section are provided on the outer circumferential face of the drum at the processing pitch in the rotational direction.

The plurality of superposed sheets (hereinafter also referred to as a "workpiece") is wrapped around the outer circumferential face of the drum, and the workpiece is continuously moved in the rotational direction of the drum along with the rotation of the drum. During such movement, the ultrasonic horn applies ultrasonic oscillation to the workpiece. When the projection section of an anvil passes through the position of the ultrasonic horn, the ultrasonic oscillation selectively acts on a portion of the workpiece where the workpiece contacts the projection section, so that that portion partially melts due to frictional heat or the like. As a result, the workpiece is welded at a predetermined processing pitch.

The stated processing pitch varies for each size of diaper product. For example, the processing pitch for an S-size (small size) diaper is small, and that for an L-size (large size) diaper is large.

For this reason, some production lines hold a sealing apparatus for each product size. In such production lines, every time the product size is changed, the sealing apparatus is replaced by a sealing apparatus of the corresponding product size, and that sealing apparatus is used.

However, holding sealing apparatuses dedicated for each product size increase the equipment cost thereof in proportion to the number of product sizes, which is an obstacle to reduction of the production cost.

The invention has been made in view of the conventional problems described above, and an advantage thereof is to provide a single-unit processing apparatus in which the processing pitch for processing performed on a continuous workpiece can be changed.

Means for Solving the Problem

In order to achieve the above-described advantages, a principal aspect of the invention is a processing apparatus that performs processing on a workpiece continuous in a transport direction while transporting the workpiece in the transport direction, and performs processing on the workpiece at a predetermined processing pitch in a rotational direction of a rotating body that rotates about an axis, during movement of the workpiece in the rotational direction by the rotation of the rotating body while the workpiece is wrapped around an outer circumferential face of the rotating body, including:

a first processing section that is disposed at a predetermined position in the rotational direction so as to oppose the outer circumferential face of the rotating body, second processing sections that are provided at each predetermined angle in the rotational direction on the outer circumferential face of the rotating body, and that perform the processing on the workpiece in cooperation with the first processing section when a second processing section opposes the first processing section, and a support section that supports the workpiece between the second processing sections, and in which it is possible to change, depending on the processing pitch, a position at which the support section supports the workpiece.

Features of the invention other than the above will become clear by reading the description of the present specification with reference to the accompanying drawings.

Effect of the Invention

According to the invention, it is possible to provide a single-unit processing apparatus in which a processing pitch for processing performed on a continuous workpiece can be changed.

BRIEF DESCRIPTION OF DRAWINGS

FIGS. 4A and 4B are explanatory diagrams of a rotating body 30 of the sealing apparatus 20; FIG. 4A illustrates a case in which a base material 1a of L size undergoes a welding process, and FIG. 4B illustrates a case in which a base material 1a of S size undergoes a welding process.

FIG. 6C This is a back view of the sealing apparatus 20a.

LIST OF REFERENCE NUMERALS

Figure 1A:
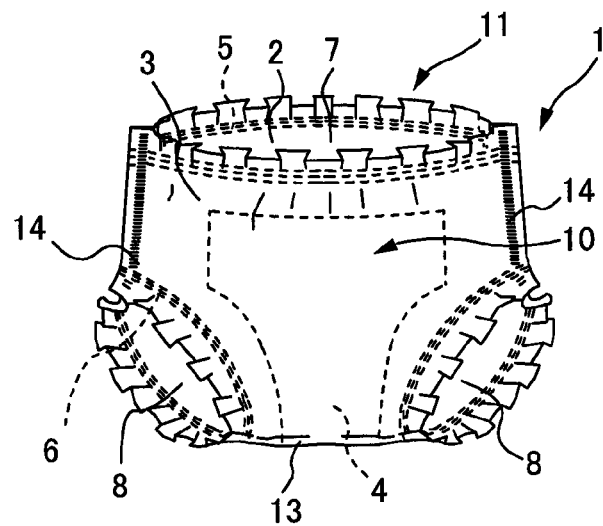
FIG. 1A is a perspective view of a finished product of a diaper 1.

1 . . . diaper, 1a . . . base material (workpiece), 2 . . . top sheet, 3 . . . back sheet, 4 . . . absorbent body, 5 . . . torso elastic member, 6 . . . leg elastic member, 7 . . . torso opening, 8 . . . leg opening, 10 . . . front face, 10a side end sections, 11 . . . back face, 11a . . . side end sections, 13 . . . crotch section, 14 . . . welding section, 15 . . . severing line, 20 . . . sealing apparatus (processing apparatus), 20a . . . sealing apparatus (processing apparatus), 22 . . . support platform, 30 . . . rotating body, 30a . . . outer circumferential face, 30b . . . unnotched section, 30c . . . notched section, 32 . . . anvil (second processing section), 32a . . . projection section, 32b . . . rib, 34 . . . support section, 34L . . . L-size support section, 34S . . . S-size support section, 36 . . . pulley, 37 . . . pulley, 41 . . . bearing member, 42a . . . guide roll, 42b . . . guide roll, 43 . . . bearing member, 44 . . . motor, 45 . . . endless belt, 46 . . . pulley, 47 . . . bearing member, 50 . . . ultrasonic horn (first processing section), 50a . . . oscillation face, 50b . . . upper end section, 52 . . . oscillation driving mechanism, 53 . . . rotating plate, 54 . . . linking rod, 54a . . . one end section, 54b . . . other end section, 56 . . . pulley, 60 . . . cutter roll (third processing section), 60a . . . outer circumferential face, 62 . . . flat blade (third blade member), 64 . . . blade rest member (fourth blade member), 68 . . . eccentric sleeve member, 70 . . . pressing belt device (holding device), 72 . . . roller, 74 . . . endless belt, CV . . . belt conveyor, R . . . support position, RL . . . support position, RS . . . support position, G . . . gap

BEST MODE FOR CARRYING OUT THE INVENTION

At least the following matters will be made clear by reading the description of the present specification with reference to the accompanying drawings.

A processing apparatus that performs processing on a workpiece continuous in a transport direction while transporting the workpiece in the transport direction, and performs processing on the workpiece at a predetermined processing pitch in a rotational direction of a rotating body that rotates about an axis, during movement of the workpiece in the rotational direction by the rotation of the rotating body while the workpiece is wrapped around an outer circumferential face of the rotating body, comprising:

a first processing section that is disposed at a predetermined position in the rotational direction so as to oppose the outer circumferential face of the rotating body, second processing sections that are provided at each predetermined angle in the rotational direction on the outer circumferential face of the rotating body, and that perform the processing on the workpiece in cooperation with the first processing section when a second processing section opposes the first processing section, and a support section that supports the workpiece between the second processing sections, and in which it is possible to change, depending on the processing pitch, a position at which the support section supports the workpiece.

With such a processing apparatus, if only one such a processing apparatus is held, it is possible to change the processing pitch of the processing performed on the workpiece, without holding processing apparatuses for each processing pitch. A detailed description will be provided below.

The above-described processing apparatus includes a support section in which it is possible to change the support position of the workpiece depending on the processing pitch. For this reason, by changing the position where the workpiece is supported, a length of a portion of the workpiece extended between the second processing sections can be changed. The processing pitch is determined based on the length of the portion of the workpiece that is extended between the second processing sections. Therefore, with the processing apparatus, it is possible to change the processing pitch of the processing on the workpiece.

In such a processing apparatus, it is preferable that a portion between the second processing sections on the outer circumferential face of the rotating body is notched, a support section is disposed at the notched portion and is detachably fixed, the support section is provided at each processing pitch, and the support section is replaced depending on the processing pitch.

With such a processing apparatus, the processing pitch can be changed with a simple method, that is, replacing the support section.

In such a processing apparatus, it is preferable that the support position of the workpiece is transferred in a radial direction of the rotating body due to replacement of the support section.

With such a processing apparatus, the processing pitch can be changed with a simple method, that is, replacing the support section.

In such a processing apparatus, it is preferable that the workpiece is made up of a plurality of superposed sheets of a thermal welding material, and the processing involves joining by welding the plurality of superposed sheets at the processing pitch.

With such a processing apparatus, the plurality of superposed sheets can be joined by welding at the processing pitch.

In such a processing apparatus, the first processing section includes an ultrasonic horn that makes ultrasonic oscillation to the workpiece, and the second processing section is an anvil including a projection section projected higher than the outer circumferential face.

In such a processing apparatus, it is preferable that a third processing section is disposed opposing the outer circumferential face of the rotating body on a downstream side of the first processing section in the rotational direction, and when the third processing section opposes the second processing section, the third processing section works in cooperation with the second processing section and severs the workpiece at the processing pitch.

With such a processing apparatus, after the workpiece that is the plurality of superposed sheets has been joined by welding at the processing pitch, it is also possible to severe the workpiece at the processing pitch for the welding.

In such a processing apparatus, the third processing section includes a third blade member, and the second processing section includes a fourth blade member that works in cooperation with the third blade member and severs the workpiece at the processing pitch.

In such a processing apparatus, it is preferable that between the first processing section and the third processing section, a holding device is provided that holds the workpiece so as to prevent the workpiece from separating from the outer circumferential face of the rotating body.

With such a processing apparatus, even if the workpiece is severed by the third processing section, the workpiece can be stably moved to the third processing section.

First Embodiment

A processing apparatus 20 according to the invention performs predetermined processing at a predetermined processing pitch on a continuous workpiece running on a continuous production line. In the first embodiment described below, a description will be given taking a base material 1a of a diaper 1 as an example of the continuous workpiece, and a welding process for welding a front face 10 of the base material 1a to a back face 11 as an example of the processing performed on the base material 1a. That is, the processing apparatus according to the first embodiment is a so-called sealing apparatus.

<<<Diaper 1 and Base Material 1a Thereof>>>

Figure 1B:
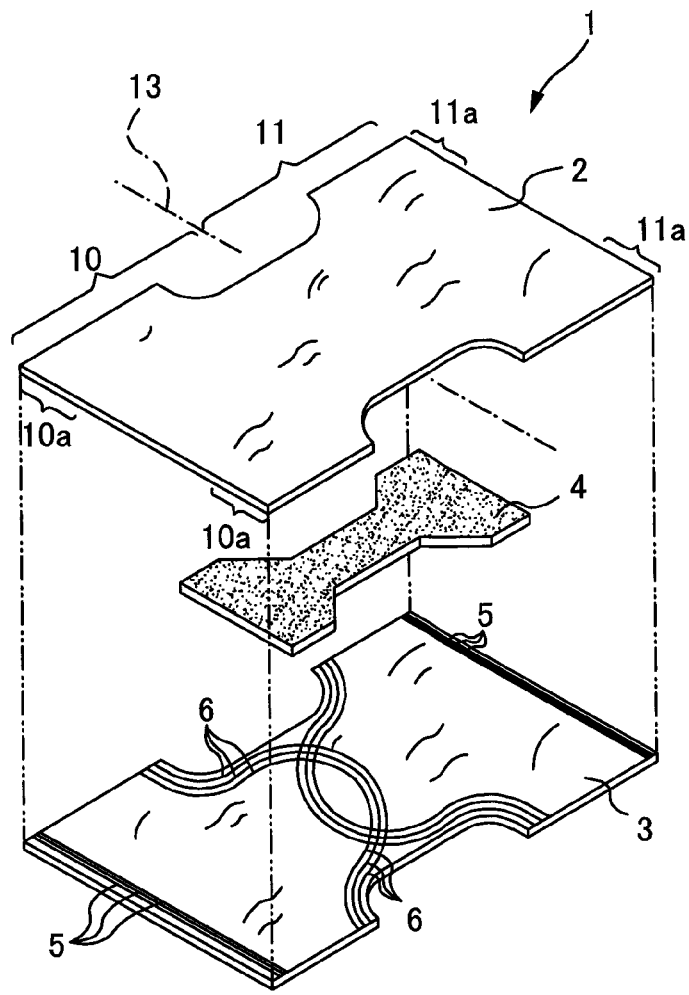
FIG. 1B is a perspective view for describing constituent elements of the diaper 1.

Firstly, the diaper 1 will be described with reference to FIGS. 1A and 1B. FIG. 1A is a perspective view of a finished product of the diaper 1. FIG. 1B is a perspective view for describing constituent elements of the diaper 1, and shows the finished product in FIG. 1A spread out in a plane at a crotch section 13 and divided into constituent elements in the thickness direction.

The diaper 1 in a spread out state shown in FIG. 1B is an accumulated sheet body formed by superposing a fluid-permeable top sheet 2, an absorbent body 4 that absorbs fluid, and a fluid-impermeable back sheet 3, in this order. As a material for the absorbent body 4, pulverized pulp in which a superabsorbent polymer is mixed is used for example. As a material for the top sheet 2 and the back sheet 3, thermoplastic resin or the like as the thermal welding material is used in the form of nonwoven fabric, woven fabric, film, or the like. The absorbent body 4 is bonded to the back sheet 3 with hot-melt adhesive or the like, and the back sheet 3 and the top sheet 2 are also bonded to each other with hot-melt adhesive or the like.

The accumulated sheet body is folded in two while placing the top sheet 2 inside and using the crotch section 13 as the folding position. In this twofold state, one side of the superposed sheets serves as the front face 10, and the other side serves as the back face 11. These front face 10 and back face 11 are joined welded to each other at welding sections 14, which are formed in side end sections 10a and 11a around a torso. In this manner, the finished product shown in FIG. 1A in which a torso opening 7 and a pair of leg openings 8 are formed is obtained. It should be noted that in each of the openings 7 and 8, rubber threads are affixed in an extended state onto an inner face of the back sheet 3 as a torso elastic member 5 and a leg elastic member 6, respectively. The openings 7 and 8 closely contact a torso and legs of a wearer.

Such a diaper 1 is continuously produced in the continuous production line. In other words, the base material 1a of the diaper 1 transported on the continuous production line is transported in a continuous sheet form in which the top sheet 2 and the back sheet 3 are continuous in a transport direction. After the base material 1a has undergone appropriate processing in each process in the continuous production line, the base material 1a is severed into product units in the transport direction in a final process, thereby becoming a finished product 1 shown in FIG. 1A.

Figure 2A:
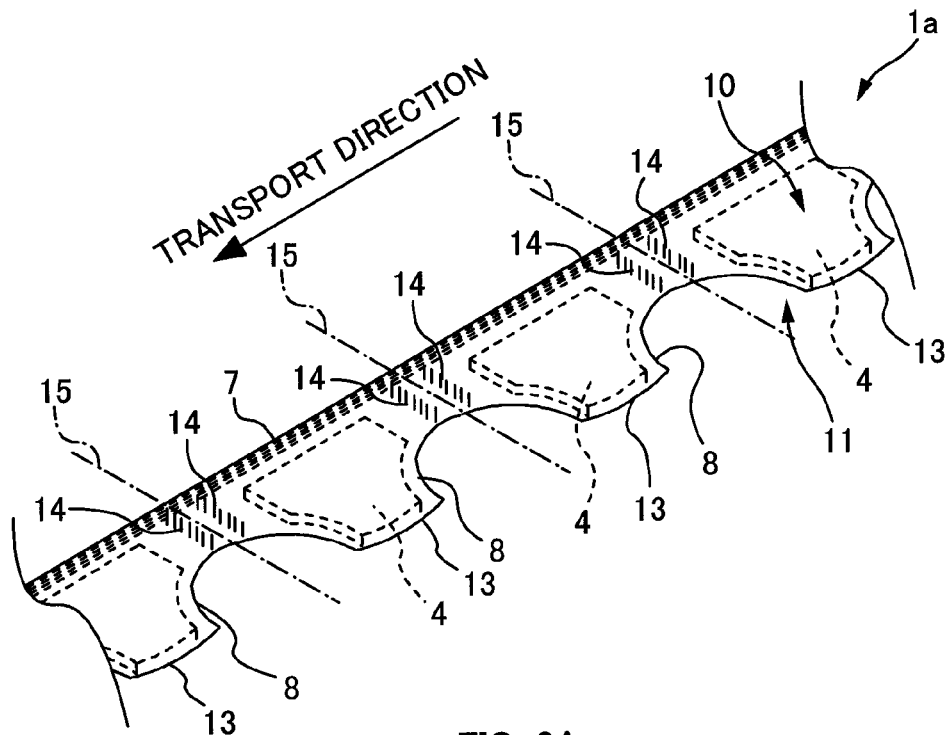
FIG. 2A is a perspective view showing a state of a base material 1a of the diaper 1 transported to a sealing process involving a sealing apparatus 20.
Figure 2B:
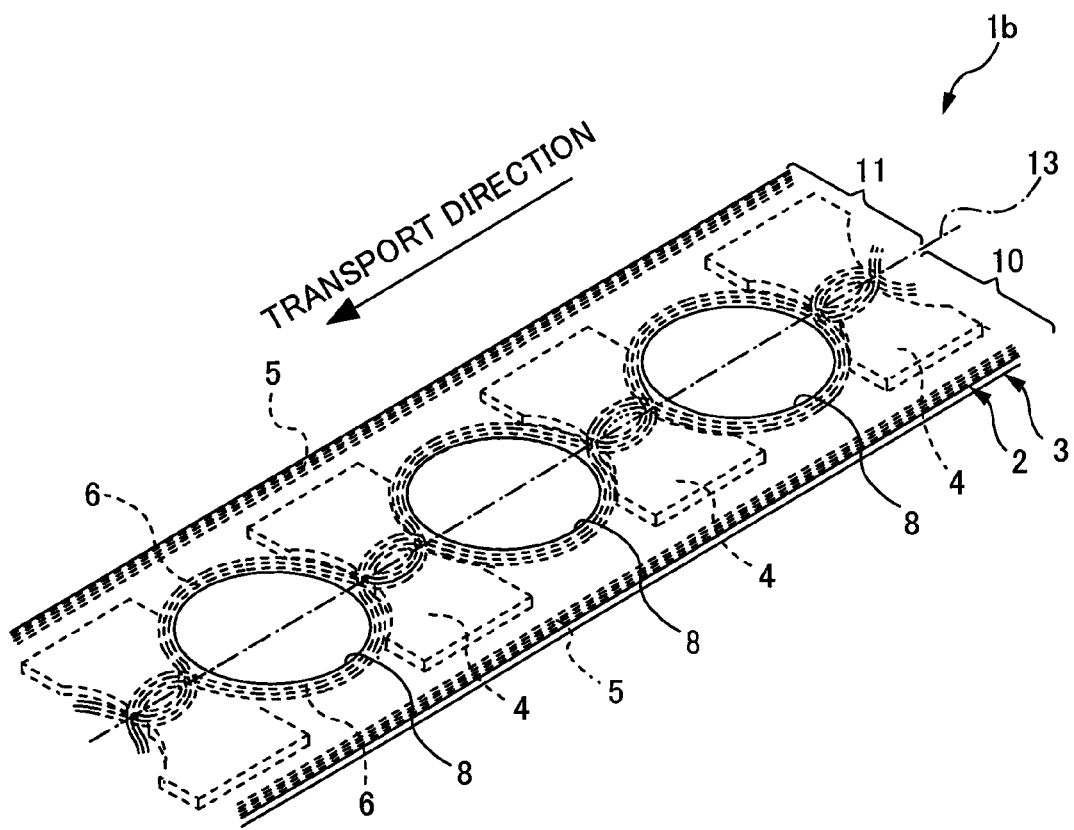
FIG. 2B is a perspective view showing a state of the base material 1a in FIG. 2A immediately before undergoing the sealing process.

FIG. 2A is a perspective view showing a state of the base material 1a of the diaper 1 transported to a sealing process involving the sealing apparatus 20. FIG. 2B is a perspective view showing a state of the base material 1a in FIG. 2A immediately before undergoing the sealing process.

The base material 1a at the point of transportation to the sealing process is in the following state: a thing 1b, as shown in FIG. 2B, in which the absorbent body 4 is sandwiched between the continuous sheets of both the top sheet 2 and the back sheet 3 and affixed at a product pitch in the transport direction, is folded in two using the crotch section 13 as the folding position, the crotch section 13 being substantially at a center in a width direction of the thing 1b. Consequently, the base material 1a is in the state shown in FIG. 2A, in which the front face 10 and the back face 11 are superposed in a vertical direction. At this stage, the leg opening 8 has been already formed between the absorbent bodies 4 and 4 adjacent in the transport direction, as shown in FIG. 2B. The leg elastic member 6 is affixed along these leg opening 8 and the crotch section 13. Also, the torso elastic member 5 is affixed along the end sections that correspond to the torso opening 7.

However, in the base material 1a in the state shown in FIG. 2A, the front face 10 and the back face 11 have not been joined to each other. Therefore, the sealing apparatus 20 performs a welding process on the base material 1a at portions corresponding to the side end sections 10a and 11a around the torso so as to form the welding section 14, thereby joining the front face 10 and the back face 11 of the base material 1a to each other. Then, the sealing apparatus 20 forwards the result to the next process. Note that a pair of welding sections 14 is formed at positions adjacent to each other in the transport direction. Then, the base material 1a is severed along a severing line 15 between this pair of welding sections 14 to become the above-stated finished product 1.

<<<Sealing Apparatus 20>>>

Figure 3A:
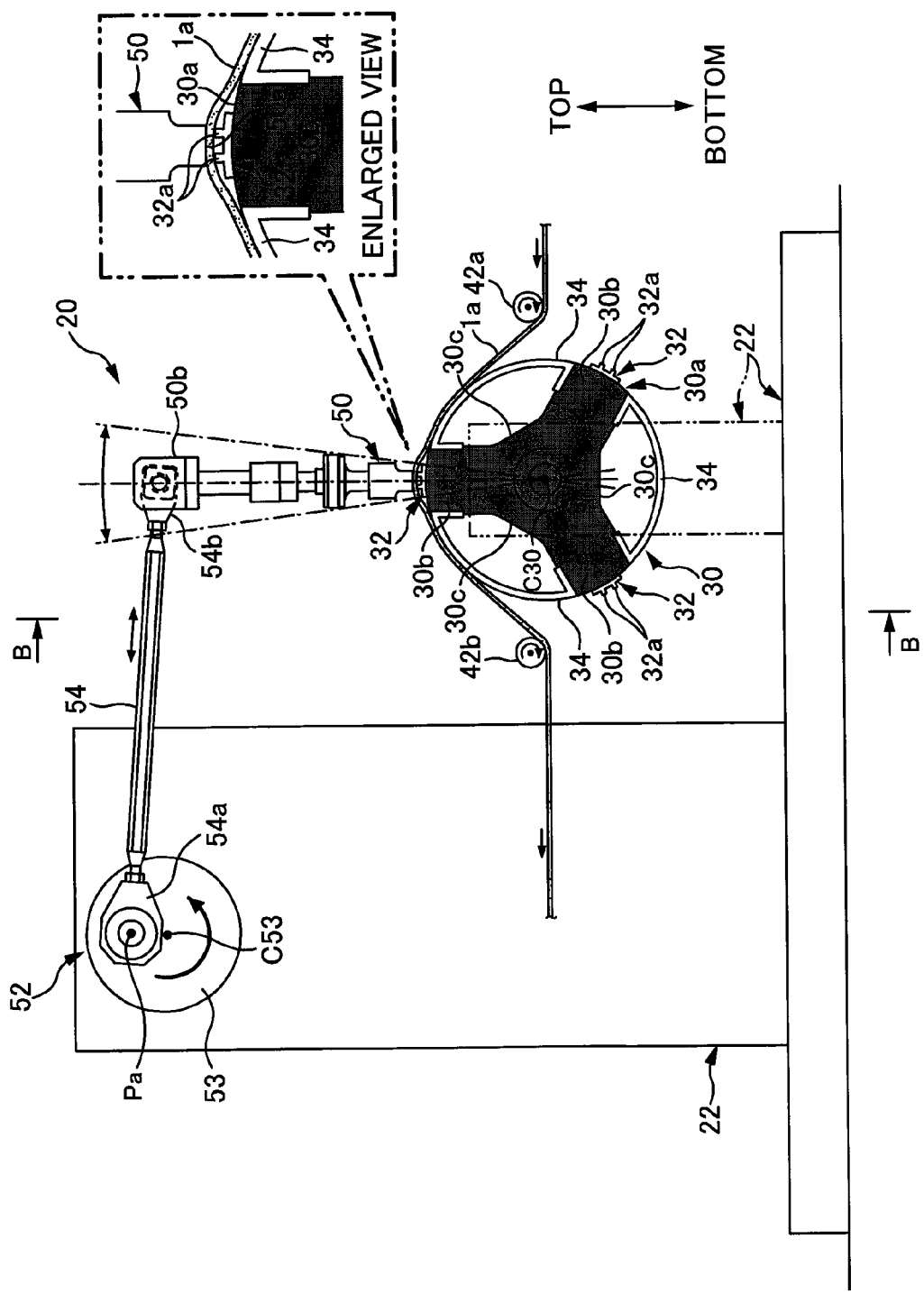
FIG. 3A This is a front view of a sealing apparatus 20 of a first embodiment.
Figure 3B:
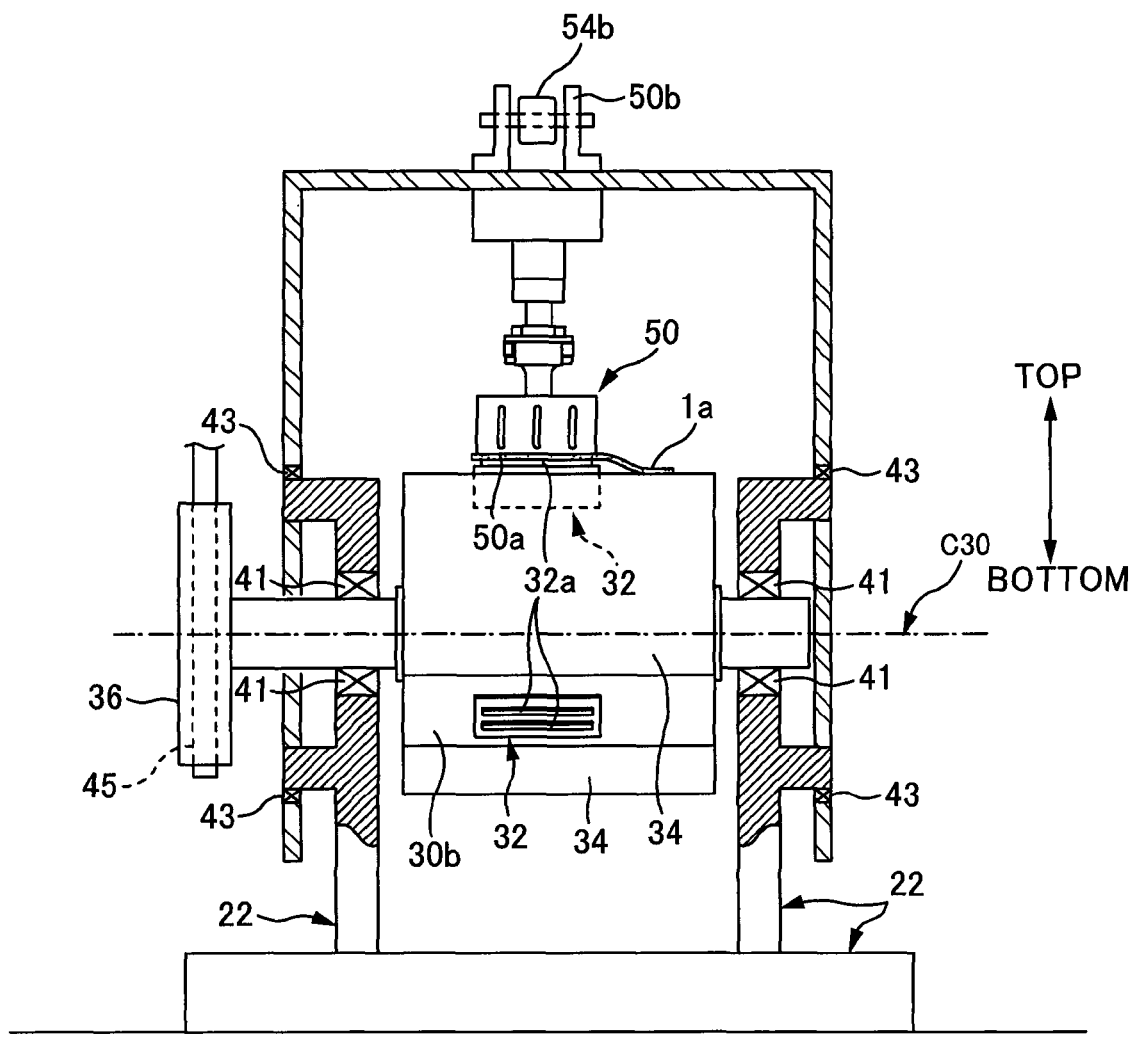
FIG. 3B This is a view taken along line B-B in FIG. 3A as viewed from the arrow side.
Figure 3C:
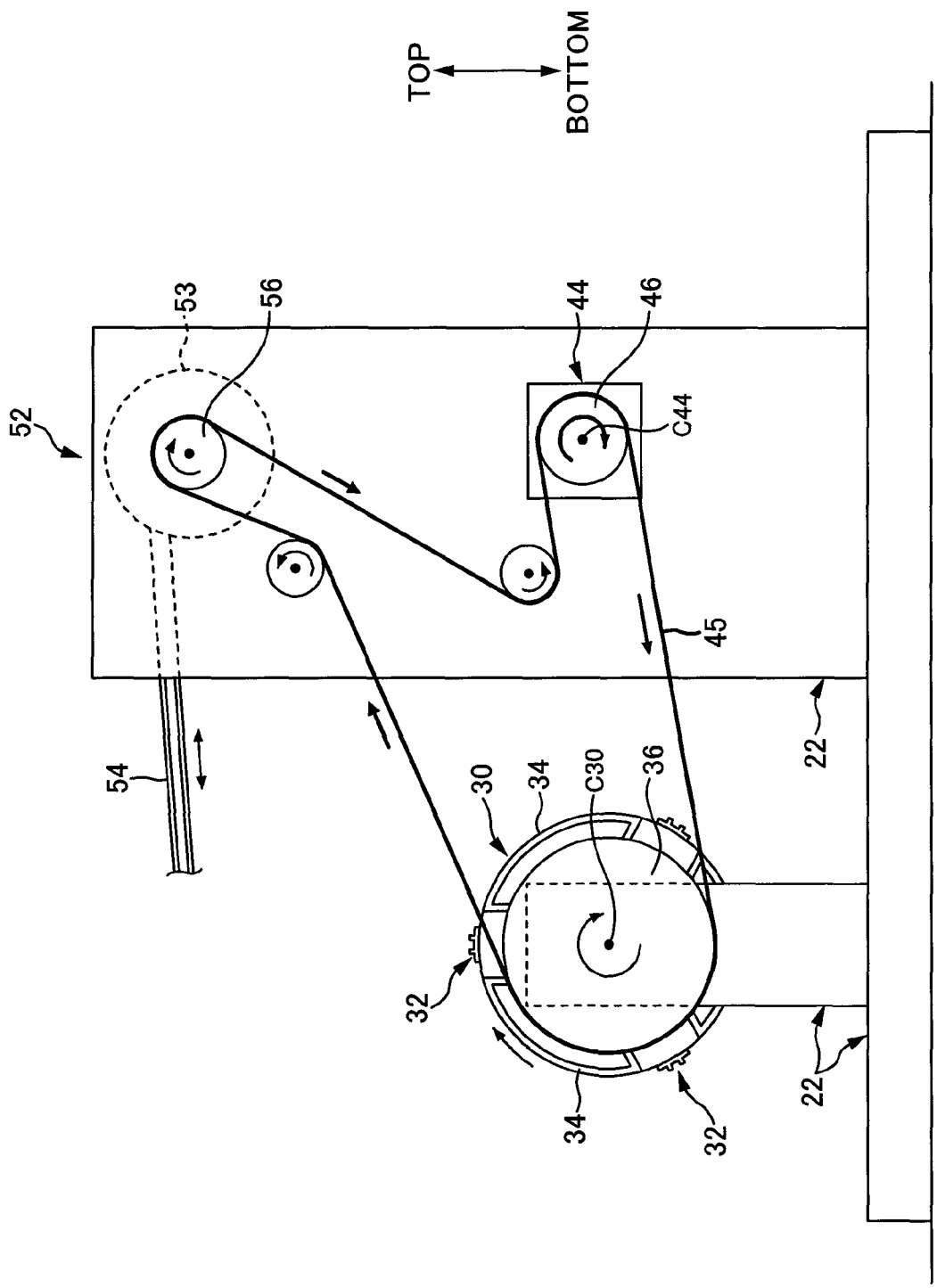
FIG. 3C This is a back view of the sealing apparatus 20.

FIG. 3A is a front view of the sealing apparatus 20. FIG. 3B is a view taken along line B-B in FIG. 3A as viewed from the arrow side. FIG. 3C is a back view of the sealing apparatus 20. In FIG. 3B, part of the sealing apparatus 20 is shown as a broken-out section. FIGS. 4A and 4B are explanatory diagrams of a rotating body 30 of the sealing apparatus 20. FIG. 4A illustrates a case in which the base material 1a of L size undergoes a welding process. FIG. 4B illustrates a case in which the base material 1a of S size undergoes a welding process.

As shown in FIGS. 3A and 3B, the sealing apparatus 20 includes the rotating body 30 that is driven and rotates while being rotatably supported by a support platform 22 via a bearing member 41, and an ultrasonic horn 50 (corresponding to a first processing section) that is disposed at a predetermined position in a rotational direction of the rotating body 30 and that opposes an outer circumferential face 30a of the rotating body 30. Anvils 32 (corresponding to a second processing section) are provided on the outer circumferential face 30a of the rotating body 30 at an interval of a predetermined angle in the rotational direction. Each anvil 32 includes a projection section 32a in the shape of the pair of welding sections 14, which projects radially outward than the outer circumferential face 30a.

As shown in FIG. 3A, the base material 1a of the diaper 1 is wrapped around the outer circumferential face 30a of the rotating body 30 at a predetermined wrapping angle, by a guide roll 42a on a upstream side and a guide roll 42b on a downstream side. With being driving and rotating of the rotating body 30, the base material 1a is moved in the rotational direction of the rotating body 30 with almost no slippage on the outer circumferential face 30a; then, the ultrasonic horn 50 applies ultrasonic oscillation to the base material 1a during such movement. This ultrasonic oscillation selectively acts on a portion of the base material 1a where the base material 1a contacts the projection section 32a of the anvil 32. Therefore, when the projection section 32a of the anvil 32 opposes the ultrasonic horn 50 during the above-stated movement in the rotational direction, the portion of the base material 1a where the base material 1a contacts the projection section 32a is selectively melted by the ultrasonic oscillation, so that the pair of welding sections 14 is formed. Specifically, the pair of welding sections 14 is formed in the base material 1a at a processing pitch based on a length D of the base material 1a spanning between the anvils 32 adjacent to each other in the rotational direction, as shown in FIG. 4A.

However, the processing pitch varies depending on a product size of the diaper 1. For example, the processing pitch for L size is larger span than that for S size. In other words, the above-described processing pitch needs to be changed in response to a change in sizes.

In this sealing apparatus 20, a length D of the base material 1a spanning between the anvils 32 can be changed. Described in further detail, the sealing apparatus 20 includes support sections 34 where the base material 1a is supported between the anvils 32, as shown in FIG. 4A. Also, a support position R of the base material 1a can be changed in a radial direction of the rotating body 30 depending on the product size, as a result of replacing the support section 34. By changing the support position R, the length D of the base material 1a spanning between the anvils 32 can be changed, and as a result thereof, the processing pitch is changed. Each of the constituent elements of the sealing apparatus 20 will be described below.

(1) Rotating Body 30

As shown in FIGS. 3A and 3B, the rotating body 30 is a member that rotates about a rotational axis C30 oriented in a horizontal direction. For example, the rotating body 30 has, as a main body, a member obtained by notching the outer circumferential face of a cylindrical body whose cross section is a perfect circle, in the same concave shape at every predetermined angle in the rotational direction. In the example of FIG. 3A, the rotating body 30 is notched in a substantially fan shape in three positions at every 120 degrees in the rotational direction, and portions 30b that have not notched remain in three positions in a state protruding in the radial direction (see portions expressed dark in FIG. 3A). On an outer circumferential face of each of these portions 30b that have not been notched in the rotating body 30 (hereinafter referred to as "unnotched sections 30b"), an anvil 32 is provided. On each of the notched portions 30c (hereinafter referred to as "notched sections 30c"), the support section 34 is disposed.

Figure 5:
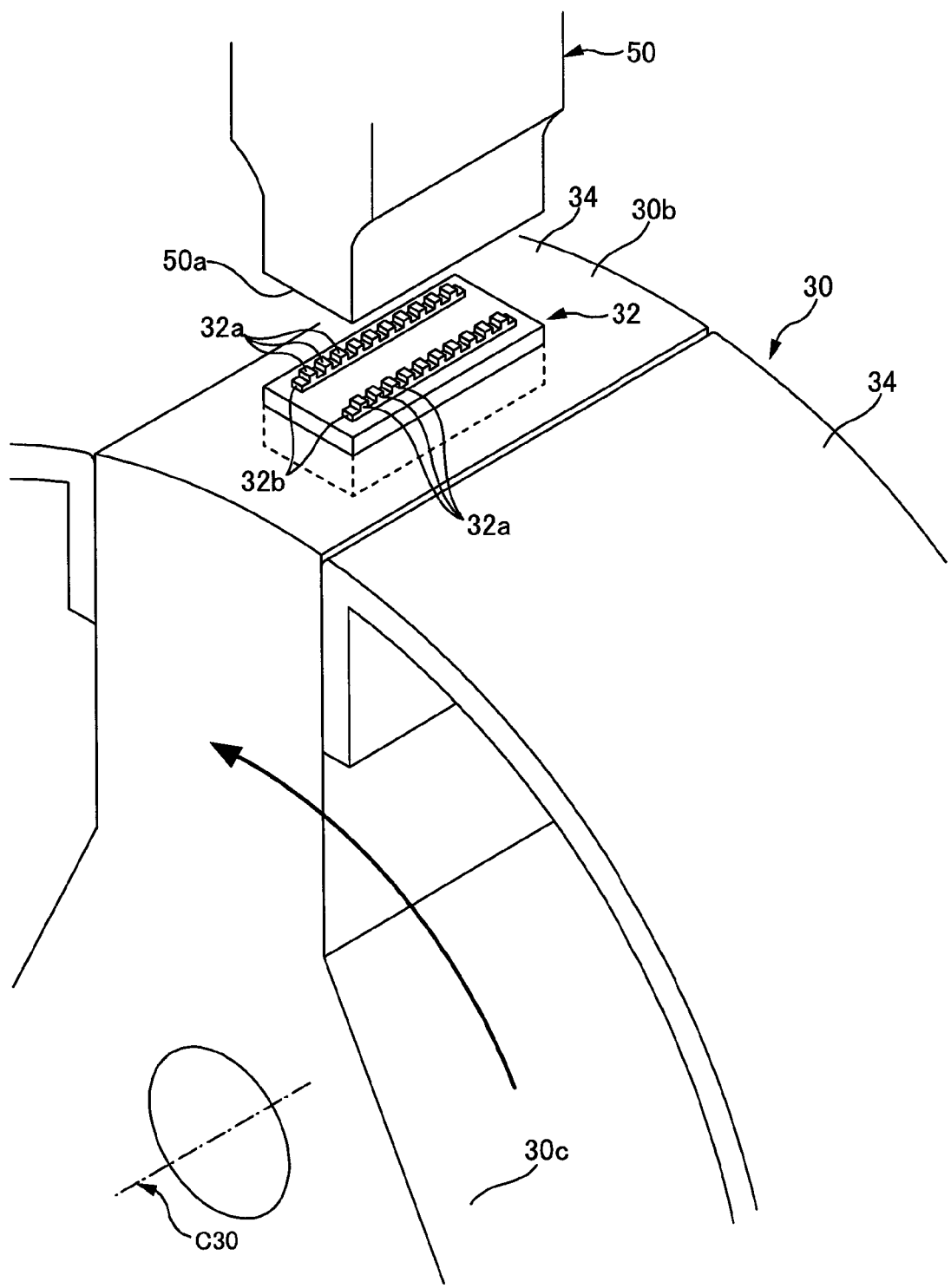
FIG. 5 This is a perspective view of an anvil 32.

FIG. 5 is a perspective view of an anvil 32. The anvil 32 is a block-shaped member, and is fitted into an indentation section in the outer circumferential face of the unnotched section 30b and is fixed with screws or the like. A pair of ribs 32b that is substantially aligned with a rotational axis direction is formed on a surface of the anvil 32 so as to correspond to a shape pattern of the pair of welding sections 14. A plurality of projection sections 32a are formed on a surface of each rib 32b, and the projection sections 32a are lined up at a predetermined pitch in a longitudinal direction of the rib 32b.

These projection sections 32a work in cooperation with the ultrasonic horn so as to form the pair of welding sections 14 in the base material 1a of the diaper. For this purpose, a top surface of each projection section 32a projects radially outward than the outer circumferential face of the unnotched section 30b, so that the base material 1a is held between the projection section 32a and the ultrasonic horn 50 to reliably transmit the ultrasonic oscillation to the base material 1a.

On the other hand, the support section 34 is a substantially arc-shaped member provided so as to cover the notched section 30c, as shown in FIG. 3A, and is disposed such that an arc-shaped outer circumferential face thereof faces outward in the radial direction of the rotating body 30. Both end sections of the support section 34 in the rotational direction are respectively fixed with screws or the like to the unnotched sections 30b, which are adjacent on both sides to the notched sections 30c. Therefore, the support section 34 is detachable from the rotating body 30. In this fixed state, as shown in FIG. 5, an outer circumferential face of the support section 34 is continuous with substantially no gap in level to the outer circumferential face of the unnotched sections 30b.

Such a support section 34 is prepared in advance for each product size, and is replaced depending on the product size of the base material 1a to be processed in accordance with the production schedule of the diaper 1. For example, in this first embodiment, as shown in FIGS. 4A and 4B, an L-size support section 34L and an S-size support section 34S are prepared capable of being replaced by each other. The L-size support section 34L shown in FIG. 4A is an arc-shaped member whose radius of curvature at an external contour is approximately the same as a radius of the unnotched section 30b of the rotating body 30. On the other hand, the S-size support section 34S shown in FIG. 4B is an arc-shaped member whose radius of curvature at an external contour is larger than a radius of curvature of the L-size support section 34L. Therefore, as clearly understood by comparing FIGS. 4A and 4B, a support position RS of the base material 1a by the S-size support section 34S is positioned further inward in the radial direction than a support position RL for the base material 1a by the L-size support section 34L. In this manner, when the S-size support section 34S is mounted to the rotating body 30, a length DS of the base material 1a spanning between the anvils 32 is shorter than a length DL of when the L-size support section 34L is mounted. As a result, the processing pitch for L size can be changed to the processing pitch for S size.

Note that although the support sections 34L and 34S shown in the drawings are both formed by bending a metal plate into an arc shape, etc., there is no limitation to this. For example, the support sections 34L and 34S may each be a block-shaped member that can be fitted into the notched section 30c of the rotating body 30. Also, the materials thereof are not limited to metal. A plastic, for example, may be used instead so long as that plastic is rigid enough not to suffer deformation caused by the wrapping force applied when the base material 1a is wrapped around the rotating body 30.

The rotating body 30 is driven with a motor 44 as a driving power source, and an endless belt power transmission device that transmits the rotational power of the motor 44 to the rotating body 30, as shown in the back view in FIG. 3C. That is, a pulley 46 is provided to a rotational axis C44 of the motor 44, and a pulley 36 is provided to the rotational axis C30 of the rotating body 30. An endless belt 45 is extended around these pulleys 46 and 36. Accordingly, when the rotational axis C44 of the motor 44 rotates, this rotational operation is transmitted to the rotating body 30 via the endless belt 45 and the like, thereby rotating the rotating body 30. The motor 44 also functions as a driving power source for the oscillation operation of the ultrasonic horn 50, which will be described later. Therefore, as shown in FIG. 3C, the endless belt 45 is extended around a pulley 56 of an oscillation driving mechanism 52 of the ultrasonic horn 50. This will be described later.

Incidentally, in the normal state of the welding process, as shown in FIG. 3A, it is often the case that while the base material 1a is continuously supplied to the sealing apparatus 20 from its upstream side at a constant transport velocity, the rotation speed (rpm) of the rotating body 30 of the sealing apparatus 20 is controlled such that the rotating body 30 rotates at a constant angular velocity corresponding to the transport velocity. In such a case, especially when the base material 1a for S size undergoes the welding process, the base material 1a may periodically become slack on the upstream side of the sealing apparatus 20. The cause of this is as described below. As described above, even when the rotating body 30 rotates at a constant angular velocity, in the case of S size shown in FIG. 4B, a wrapping radius of the base material 1a that is wrapped around the outer circumferential face of the rotating body 30 differs between at a position of the anvil 32 and a position of the support section 34S; as a result, the moving velocity of the base material 1a when the base material 1a is drawn to be wrapped around the rotating body 30 fluctuates on a periodical basis. Such periodic fluctuation of the moving velocity sometimes does not appear as the above-mentioned slackness as a result of such fluctuation being naturally absorbed due to elastic deformation of the base material 1a. However, a device for absorbing the slackness in the base material 1a is preferably disposed on the upstream side of the sealing apparatus 20. A so-called dancer roll (a roll guided for translational movement, which performs translational operation so as to adjust a tension of the base material 1a wrapped around this roll to a desirable tension) is an example of such a device.

(2) Ultrasonic Horn 50

As shown in FIG. 3A, the ultrasonic horn 50 is disposed above the rotating body 30 (in FIG. 3A, twelve-o'clock position on the clock face). A bottom face 50a of the ultrasonic horn 50 opposes the outer circumferential face 30a of the rotating body 30, and an oscillation face 50a for ultrasonic oscillation is provided in the bottom face 50a. From this oscillation face 50a, ultrasonic oscillation is continuously emitted to the base material 1a. Therefore, when the projection section 32a of the anvil 32 passes through a position of the oscillation face 50a along the rotational direction, a portion that is included in the base material 1a and that is sandwiched between the oscillation face 50a and the projection section 32a is selectively melted with the ultrasonic oscillation. In this manner, the pair of welding sections 14 is formed in the base material 1a.

As shown in FIGS. 3A and 3B, the ultrasonic horn 50 is supported by bearing members 43 of the support platform 22 capable of revolving while having the rotational axis thereof intersecting the rotational axis C30 of the rotating body 30. The ultrasonic horn 50 is configured to sway back and forth once in the rotational direction each time the rotating body 30 rotates by the processing pitch. This is for securing a long adhesion time. That is, when the projection section 32a of the anvil 32 passes through the ultrasonic horn 50, the ultrasonic horn 50 is moved in the same direction as the rotational direction of the rotating body 30. As a result thereof, the relative velocity difference in the rotational direction is reduced between the projection section 32a of the anvil 32 and the ultrasonic horn 50, thereby securing a sufficient adhesion time. Accordingly, while the ultrasonic horn 50 moves in a forward direction in the rotational direction when the projection section 32a of the anvil 32 passes through the ultrasonic horn 50, once the projection section 32a of the anvil 32 has passed through the ultrasonic horn 50, the ultrasonic horn 50 reverses its moving direction and moves in a backward direction until the ultrasonic horn 50 returns to a start position for a next forward movement. Such an operation of swaying back and forth is repeatedly performed for each anvil 32 (three anvils 32 in the drawings) included in the rotating body 30.

As the oscillation driving mechanism 52 that performs this swaying operation, for example, a crank mechanism that converts rotational movement to a back and forth movement as shown in FIG. 3A is used. Specifically, the oscillation driving mechanism 52 includes a rotating plate 53 that is driven and rotates, and a linking rod 54 whose one end section 54a is linked to a position Pa, which is eccentric to a rotational center C53 of the rotating plate 53. The other end section 54b of the linking rod 54 is linked to the upper end section 50b of the ultrasonic horn 50. Therefore, when the rotating plate 53 performs one rotation, the linking rod 54 is moved back and forth in a longitudinal direction thereof only once. With this back and forth movement, the ultrasonic horn 50 performs the operation of swaying back and force only once.

The driving power source of the rotating plate 53 is the motor 44, which is the same motor 44 that drives the rotating body 30. The same driving power source is used because it is necessary to synchronize the rotational operation of the rotating body 30 and the operation of swaying back and forth of the ultrasonic horn 50. Therefore, as shown in FIG. 3C, the pulley 56 is fixed to the rotating plate 53 and the endless belt 45 for driving the rotating body 30 is extended around the pulley 56. A ratio of a diameter of the pulley 56 of the rotating plate 53 to a diameter of the pulley 36 of the rotating body 30 is set to the multiplicative inverse of the number of the provided anvils 32, such that while the rotating body 30 performs one rotation, the ultrasonic horn 50 performs the operation of swaying back and forth on a periodical basis for the number of the anvils 32 provided in the rotating body 30. For example, since the number of the anvils 32 provided in the rotating body 30 is three, the diameter of the pulley 56 of the rotating plate 53 is set to one-third of the diameter of the pulley 36 of the rotating body 30. In this manner, the ultrasonic horn 50 reliably performs the operation of swaying back and forth on each anvil 32. Note that, in the present embodiment, the endless belt 45 for driving is extended around as a means for achieving synchronization. However, the rotating body 30 and the ultrasonic horn 50 may be separately driven with a servo motor or the like, and the operations thereof may be synchronized electrically.

(3) Effects

Effects of the sealing apparatus 20 will be described here.

First, this sealing apparatus 20 can cope with changing sizes by simply replacing the support section 34 shown in FIG. 3A, which means that replacing the sealing apparatus 20 as a whole is not required. As a result, the followings are not required: (a) the equipment cost can be reduced since holding the sealing apparatus 20 for each product size can be avoided, (b) work load for changing the size can be reduced, (c) space for storing the sealing apparatus 20 for various product sizes can be reduced, and (d) apparatuses for simplifying work for replacing the sealing apparatus 20 (for example, a slide-type cradle, a hoist crane, or a lifting device).

Also, regardless of the size change, a rotational radius of the top surface of the projection section 32a of the anvil 32 of the rotating body 30 remains unchanged. Therefore, when the rotating body 30 rotates at a constant angular velocity, the circumferential velocity of the projection section 32a of the anvil 32 is constant regardless of the size change. A position, in the radial direction, of the top surface of the projection section 32a of the anvil 32 of the rotating body 30 is unchanged, and a phase relation between the rotational operation of the rotating body 30 and the operation of swaying back and forth of the ultrasonic horn 50, is also unchanged. Therefore, regardless of the product size, conditions for the welding process (for example, conditions relating to the welding time, such as relative difference in velocity when the anvil 32 passes through the ultrasonic horn 50) are constant. As a result, adjustment work is not required for the anvil 32 and the ultrasonic horn 50 due to the size change (for example, adjustment work relating to the stated relative difference in velocity).

Second Embodiment

Figure 6A:
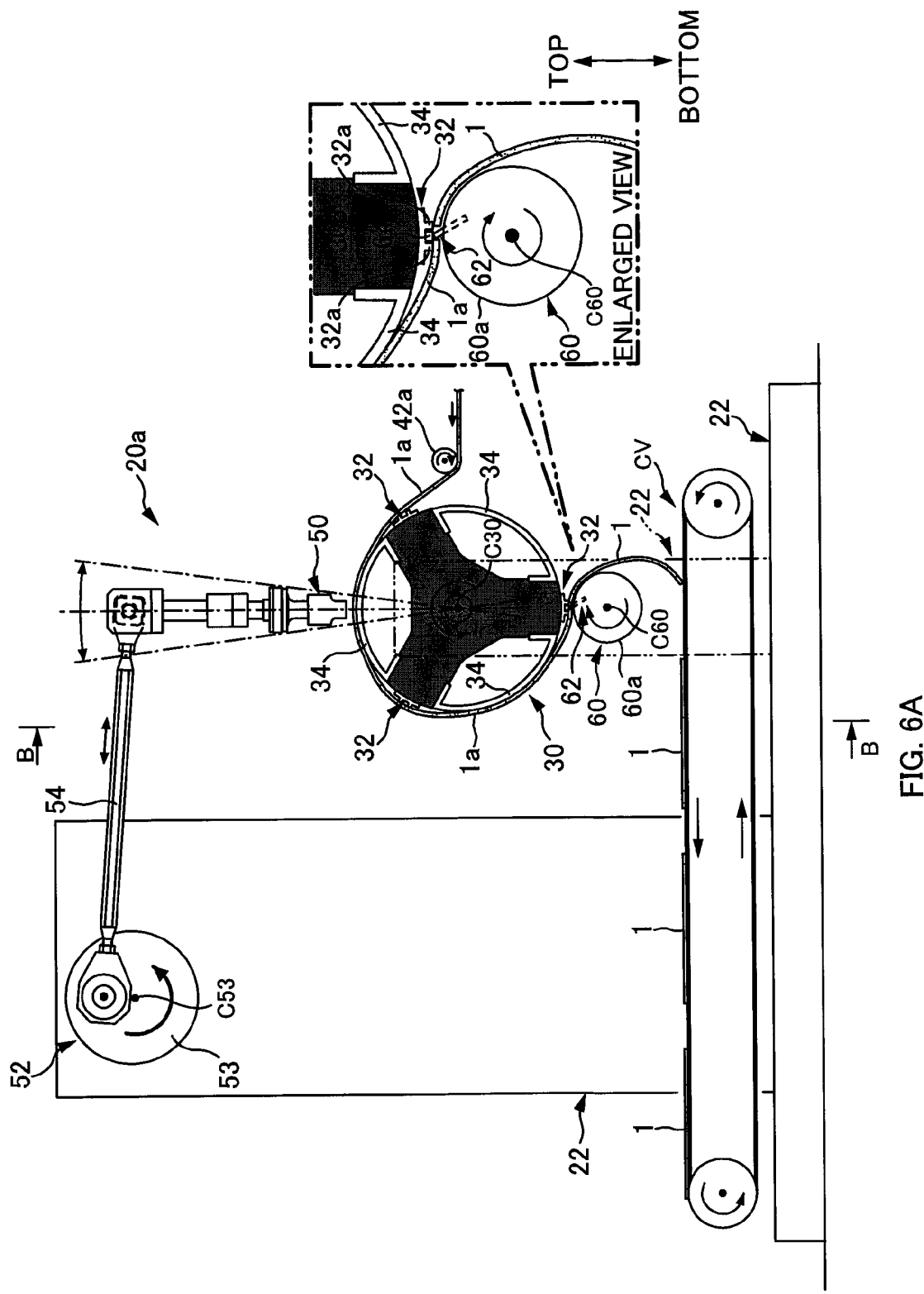
FIG. 6A This is a front view of a sealing apparatus 20a of a second embodiment.
Figure 6B:
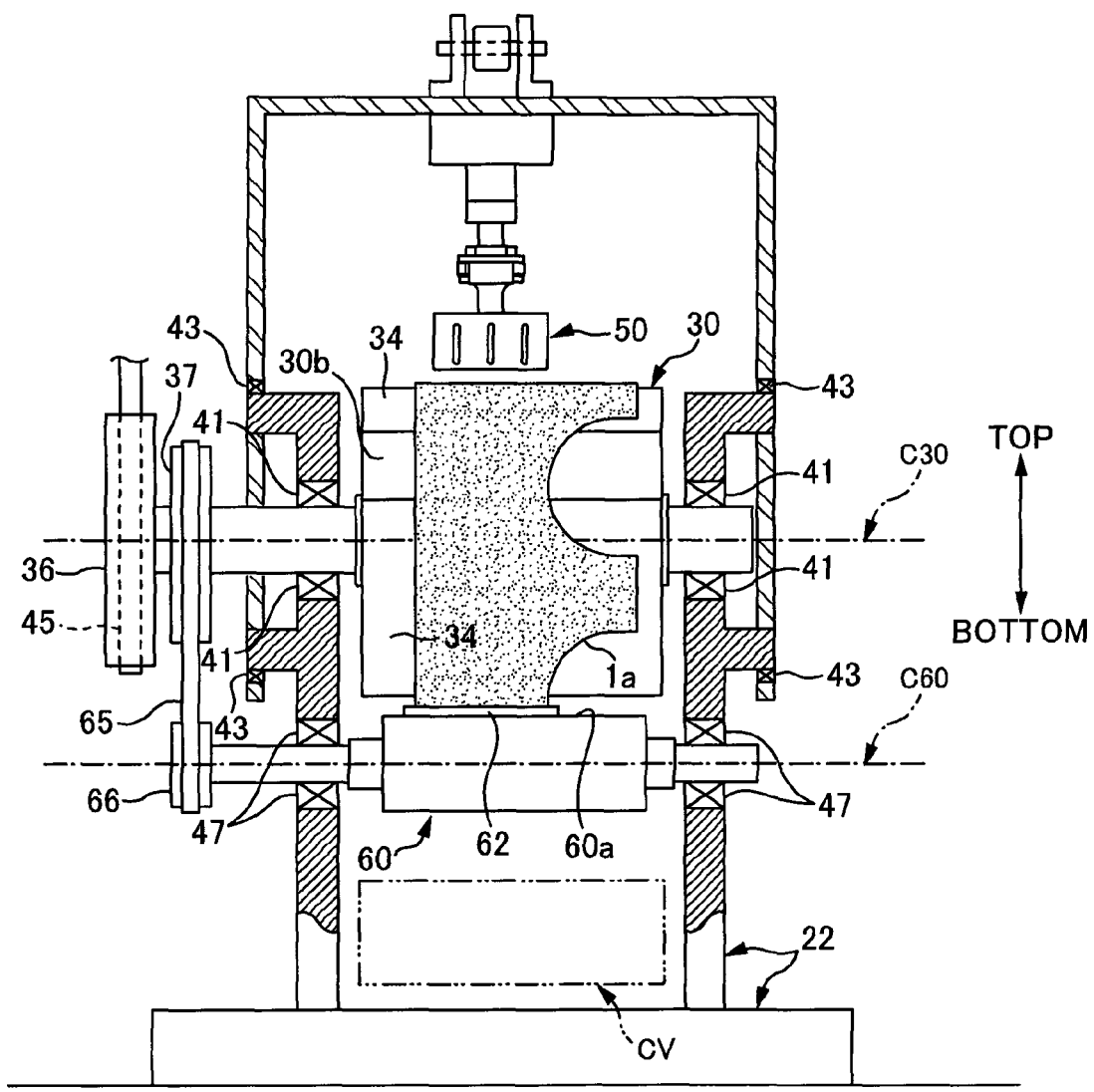
FIG. 6B This is a view taken along line B-B in FIG. 6A as viewed from the arrow side.
Figure 6C:
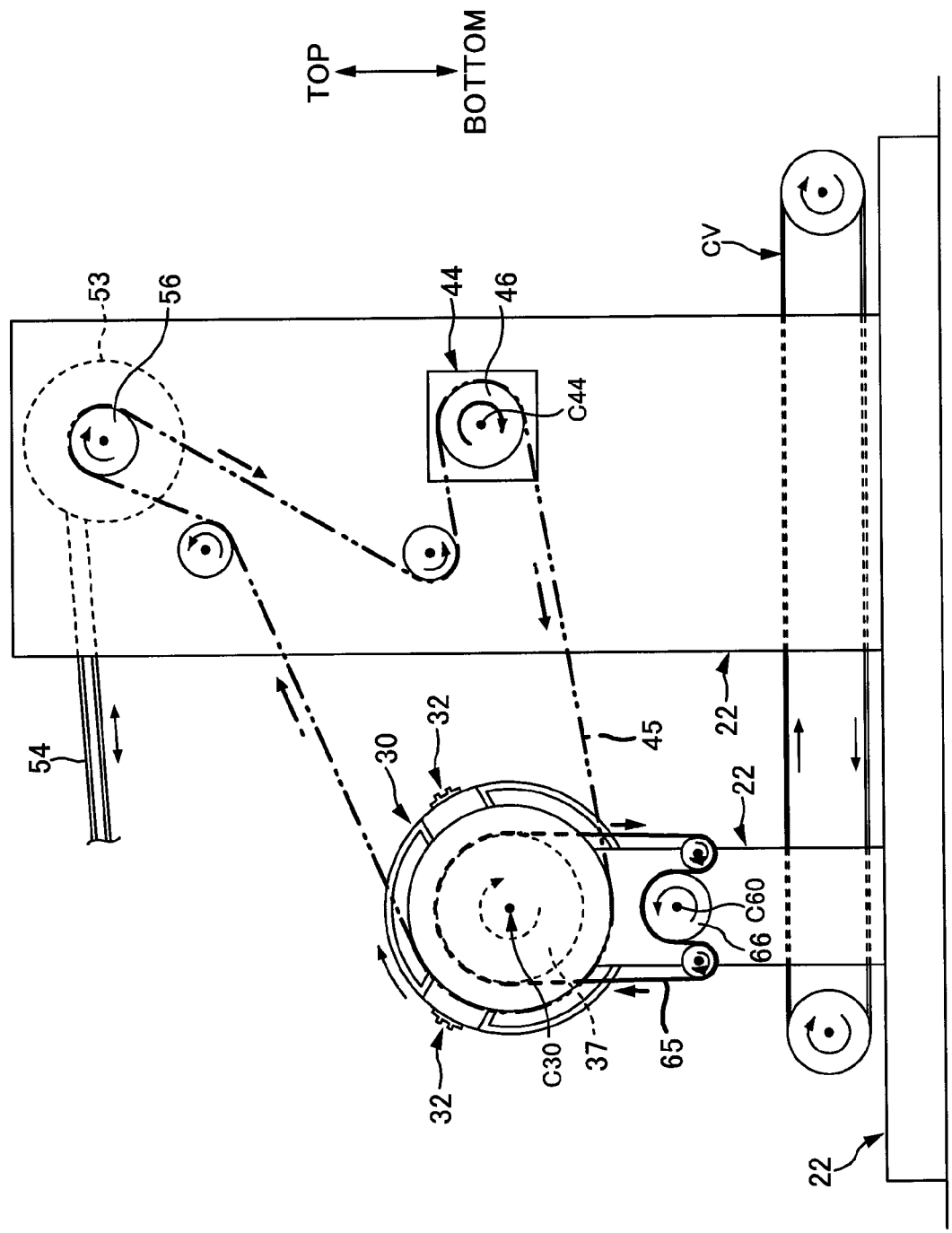

FIG. 6A is a front view of a sealing apparatus 20a of a second embodiment. FIG. 6B is a view taken along line B-B in FIG. 6A as viewed from the arrow side. FIG. 6C is a back view of the sealing apparatus 20a. In FIG. 6B, part of the sealing apparatus 20a is shown as a broken-out section.

The sealing apparatus 20 according to the above-described first embodiment performs the welding process only. However, the sealing apparatus 20a according to the second embodiment differs from the first embodiment in that the sealing apparatus 20a performs the welding process and in addition, a severing process for severing into product units the base material 1a of the diaper 1 that has undergone the welding process. Specifically, a cutter roll 60 (corresponding to a third processing section) is additionally provided for the severing process at a predetermined position on the further downstream side in the rotational direction than the ultrasonic horn 50 (in FIG. 6A, six-o'clock position on the clock face). Below the cutter roll 60, a belt conveyor CV is additionally provided that receives diapers 1 of product units, which fall after being subjected to the severing process.

As shown in FIGS. 6A and 6B, the main body of the cutter roll 60 is a cylindrical body whose cross section is a perfect circle, and the cutter roll 60 is supported by bearings 47 of the support platform 22 rotatably about a rotational center C60, which is a center of the perfect circle. The orientation of the rotational center C60 is parallel to the rotational axis C30 of the rotating body 30, and as shown in FIG. 6A, the cutter roll 60 is driven and rotates in the direction of forwarding the base material 1a to the downstream side in the rotational direction of the rotating body 30. Also, flat blades 62 disposed along the rotational axis C30 at intervals of a predetermined angle in the rotational direction (corresponding to a third blade member) are provided projected on an outer circumferential face 60a of the cutter roll 60. On the rotating body 30, a blade rest member 64 (corresponding to a fourth blade member) for receiving the flat blade 62 is fixed at a portion between the pair of projection sections 32a of each anvil 32.

While the cutter roll 60 is driven and rotates together with the rotating body 30, the flat blade 62 of the cutter roll 60 opposes the blade rest member 64 of the anvil 32, and thereby the base material 1a wrapped around the rotating body 30 is severed into product units at a portion between the pair of welding sections 14.

Note that in order to cause the blade rest member 64 of the anvil 32 of the rotating body 30 and the flat blade 62 of the cutter roll 60 to perfectly oppose to each other as described above while the rotating body 30 and the cutter roll 60 respectively are driven and rotate, the cutter roll 60 and the rotating body 30 need to satisfy the following two conditions in relation to the number of provided flat blades 62 or the anvils 32, etc.

Firstly, it is necessary that the following values are approximately equal: a value obtained by dividing the circumference length of a pitch circle based on rotational radius of the blade tip of the flat blade 62 on the outer circumferential face 60a of the cutter roll 60 by the number of provided flat blades 62 of the cutter roll 60; and a value obtained by dividing the circumference length of a pitch circle based on a rotational radius of the blade rest member 64 of anvil 32 by the number of provided anvils 32 on the outer circumferential face 30a of the rotating body 30.

In addition, the cutter roll 60 is required to rotate in synchronization with the rotating body 30. Here, the rotational operation of the rotating body 30 is used as a driving power source for the cutter roll 60. Specifically, as shown in FIGS. 6B and 6C, a pulley 37 is provided in the rotating body 30 so as to have the rotational axis C30 as a rotational axis of the pulley 37. A pulley 66 is provided in the cutter roll 60 so as to have the rotational axis C60 as the rotational axis of the pulley 66. An endless belt 65 is extended around these pulleys 37 and 66 in an S form. Thereby, the rotational operation of the rotating body 30 is transmitted to the cutter roll 60 via the endless belt 65, and consequently the cutter roll 60 is driven and rotates.

However, in order to cause the flat blade 62 of the cutter roll 60 to oppose the blade rest member 64 of each anvil 32 of the rotating body 30 in a corresponding manner, it is necessary to adjust a ratio of a rotational angle of the cutter roll 60 to a rotational angle of the rotating body 30 based on a ratio between the number of the provided anvils 32 and the number of the provided flat blades 62. This adjustment is performed by setting a ratio of a diameter of the pulley 66 of the cutter roll 60 to a diameter of the pulley 37 of the rotating body 30, described above, and the ratio is set to a value obtained by dividing the number of the provided anvils 32 by the number of the provided flat blades 62. For example, in this example, three anvils 32 are provided while one flat blade 62 is provided. Therefore, the diameter of the pulley 66 of the cutter roll 60 is set to one-third of the diameter of the pulley 37 of the rotating body 30.

By satisfying the above two conditions, while the rotating body 30 and the cutter roll 60 are driven and rotates respectively, the blade rest member 64 of the anvil 32 of the rotating body 30 and flat blade 62 of the cutter roll 60 perfectly oppose each other.

Figure 7:
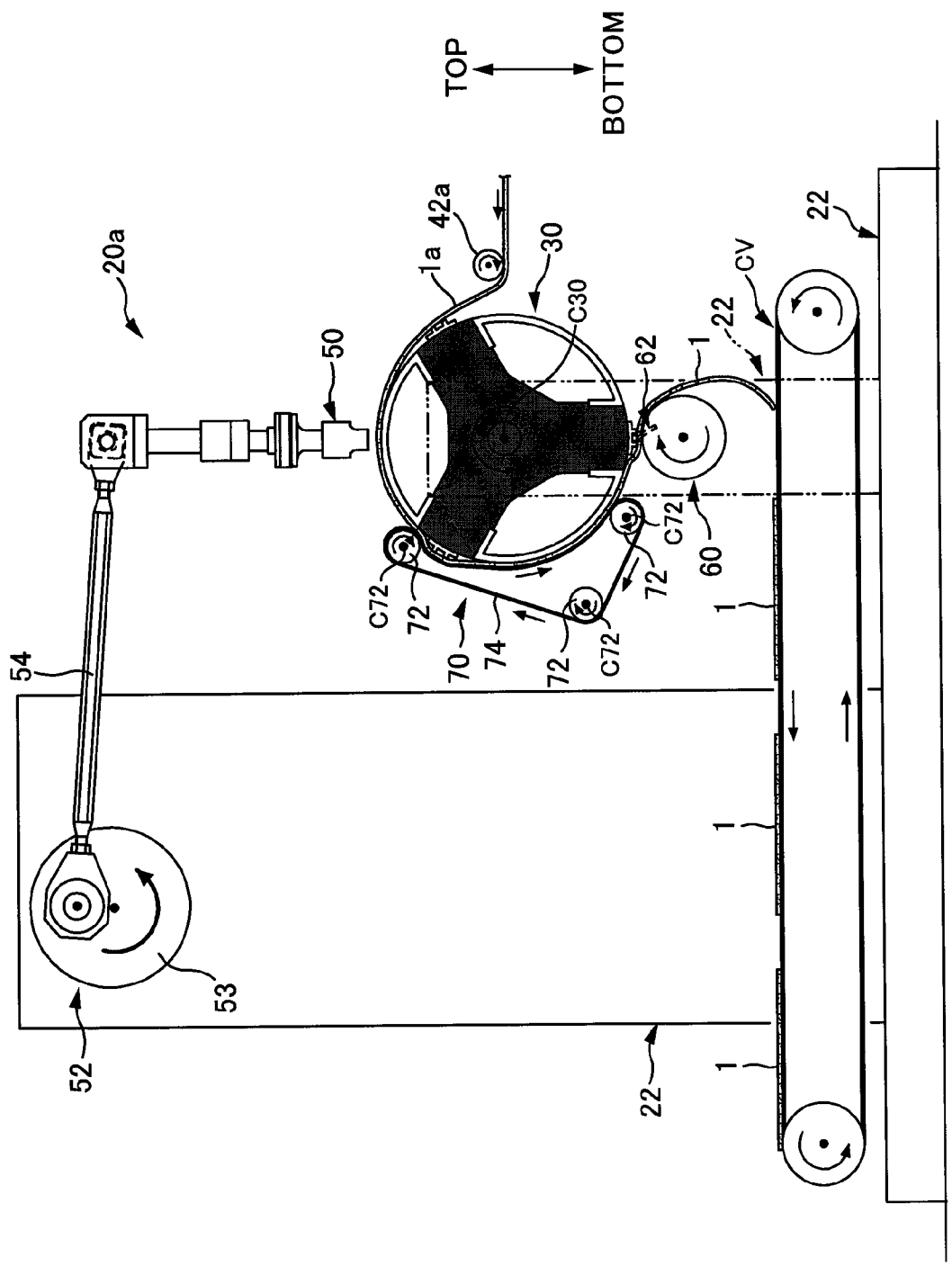
FIG. 7 This is a front view of the sealing apparatus 20a including a pressing belt device 70.

As shown in FIG. 6A, when the base material 1a is severed by the cutter roll 60, a tension necessary for the base material 1a to wrap around the rotating body 30 is lost, and the base material 1a is separated from the rotating body 30 in a range from the ultrasonic horn 50 to the cutter roll 60. As a result, there is a risk that the base material 1a will not be forwarded to a position of the cutter roll 60 in a stable manner. For this reason, it is preferable that as shown in FIG. 7, a pressing belt device 70 (corresponding to a holding device) is disposed over a portion between the ultrasonic horn 50 and the cutter roll 60 in the rotational direction of the rotating body 30. In this manner, the base material 1a is pressed against the outer circumferential face 30a of the rotating body 30, and is stably transported to the cutter roll 60.

This pressing belt device 70 includes three rollers 72 that are rotatable about a rotational axis C72 parallel to the rotational axis C30 of the rotating body 30, and an endless belt 74 extended around these three rollers 72. One of the rollers 72 is disposed on a side close to the ultrasonic horn 50 in the rotational direction, and another roller 72 is disposed on a side close to the cutter roll 60 in the rotational direction. In this manner, a portion 74a that is included in the endless belt 74 and that is positioned between these rollers 72 and 72 is pressed toward the rotating body 30, and the base material 1a is abutted against the outer circumferential face 30a of the rotating body 30 so as to be incapable of separating from the outer circumferential face 30a. Note that three rollers 72 are all driven rollers, and therefore the endless belt 74 obtains rotational power from the rotating body 30 and the base material 1a, which the endless belt 74 abuts against, and rotates with the rotating body 30 and the base material 1a.

Figure 8A:
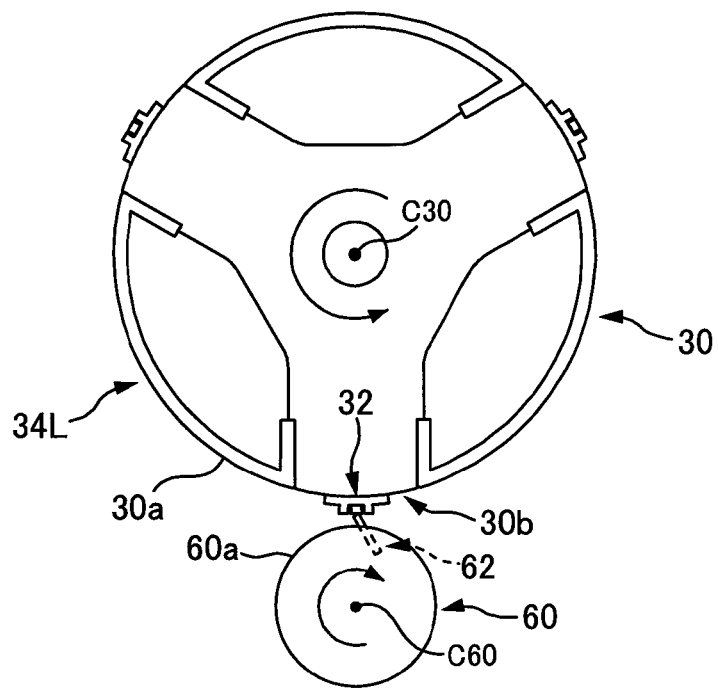
FIGS. 8A and 8B are explanatory diagrams of a gap G that can occur between an outer circumferential face 60a of a cutter roll 60 and an outer circumferential face 30a of a rotating body 30 during the welding process for L size.
Figure 8B:
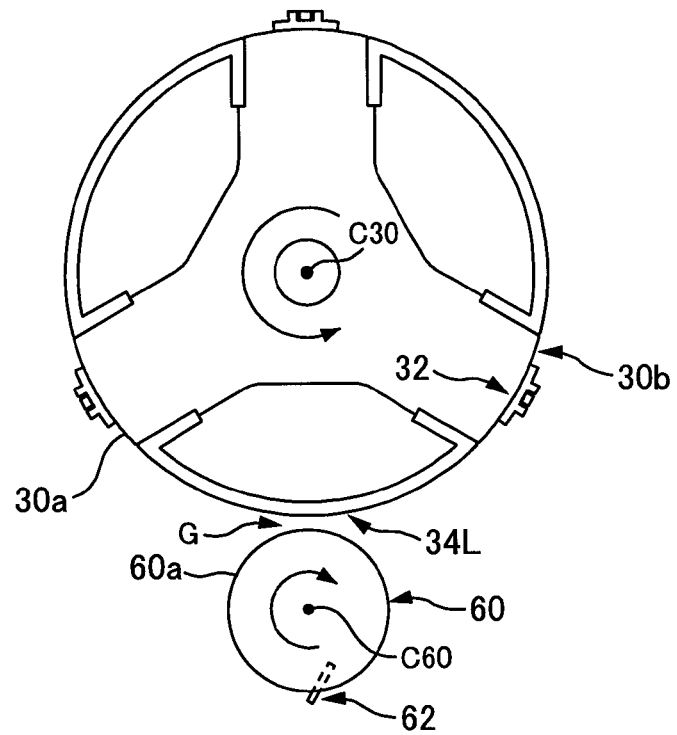
Figure 9A:
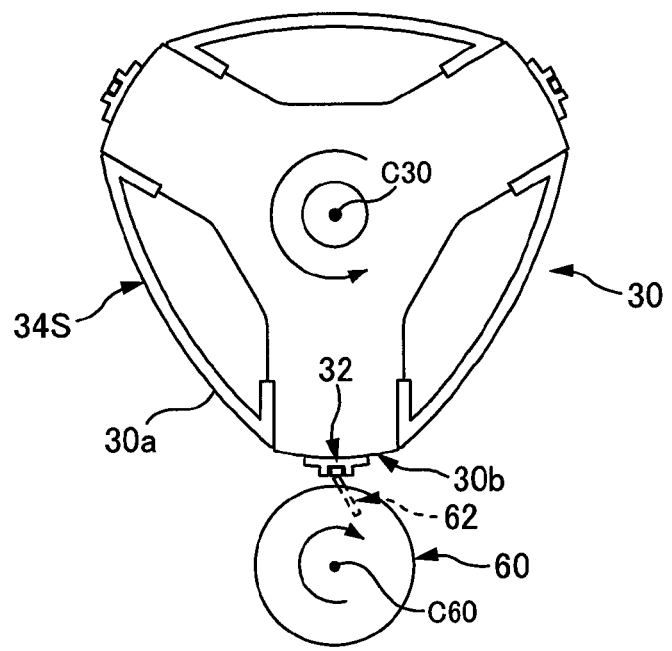
FIGS. 9A and 9B are explanatory diagrams of a gap G that can occur between an outer circumferential face 60a of a cutter roll 60 and an outer circumferential face 30a of a rotating body 30 during the welding process for S size.
Figure 9B:
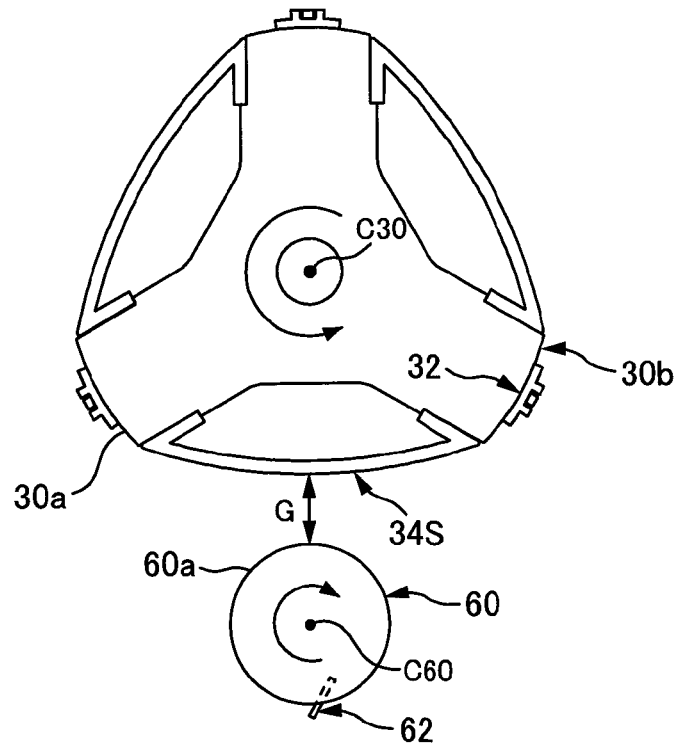

In the case of L size, as shown in FIGS. 8A and 8B, a large gap G is not created between the outer circumferential face 60a of the cutter roll 60 and the outer circumferential face 30a of the rotating body 30. However, in the case of S size, as shown in FIG. 9B, a large gap G is sometimes created between the outer circumferential face 60a of the cutter roll 60 and the outer circumferential face 30a of the rotating body 30. This is because in the case of L size shown in FIGS. 8A and 8B, a rotational diameter of the outer circumferential face of the rotating body 30 is approximately constant over the entire circumference thereof irrespective of any position of the unnotched section 30b or the support section 34L, and because in the case of S size shown in FIGS. 9A and 9B, a rotational radius in the support section 34S is smaller than a rotational radius of the unnotched section 30b. Specifically, as shown in FIG. 9B, a large gap G is created between the support section 34S and the outer circumferential face 60a of the cutter roll 60 when the support section 34S and the outer circumferential face 60a oppose to each other.

Figure 10A:
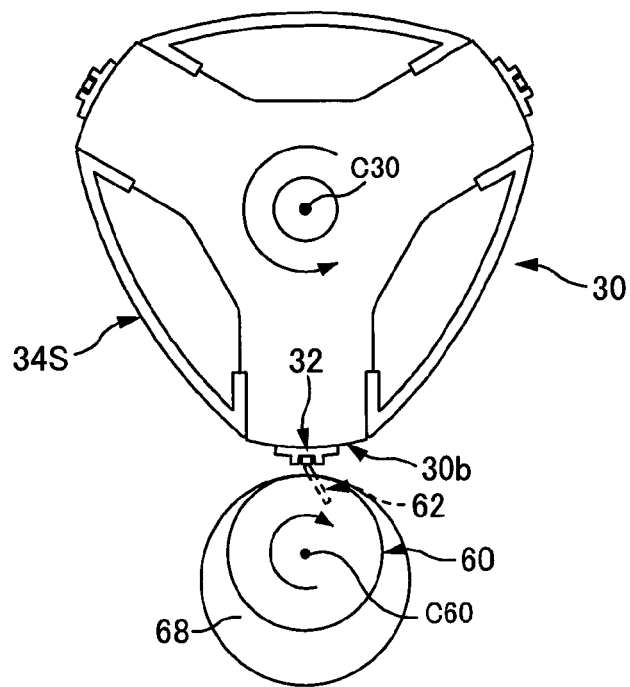
FIGS. 10A and 10B are diagrams showing a case in which an eccentric sleeve member 68 is attached to the outer circumferential face 60a of the cutter roll 60 during the welding process for S size.
Figure 10B:
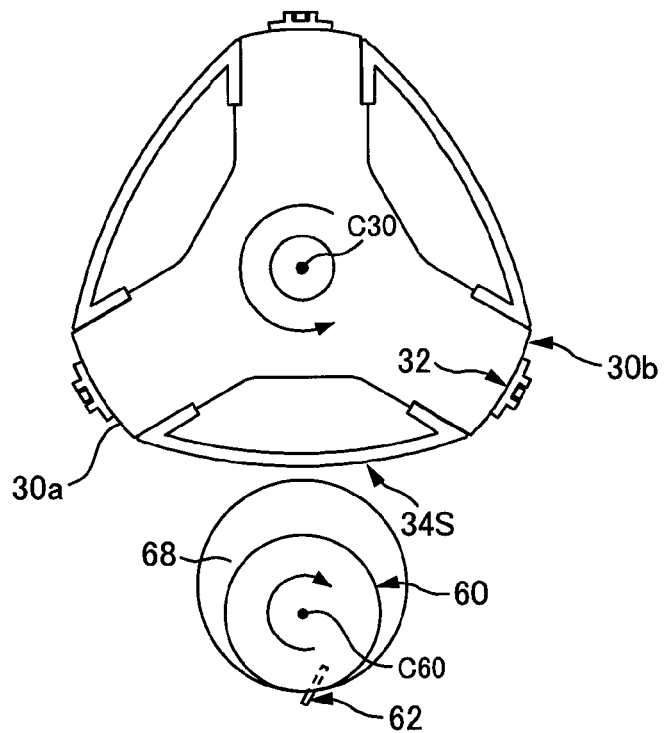

When such a gap G is created, the base material 1a separates from the outer circumferential face 30a of the rotating body 30, which interferes with stable transportation of the base material 1a to the cutter roll 60, as described in the description related to the pressing belt device 70. Thus, it is preferable that as shown in FIGS. 10A and 10B, an eccentric sleeve member 68 is detachably attached with screws or the like to the outer circumferential face 60a of the cutter roll 60, such that a rotational diameter of the eccentric sleeve member 68 increases for a range where the S-size support section 34S opposes the outer circumferential face 60a. As shown in FIG. 10A, this enables to fill the gap G between the S size support section 34S and the outer circumferential face 60a of the cutter roll 60, which is created when the S size support section 34S opposes the outer circumferential face 60a. As a result thereof, stable transportation of the base material 1a to the cutter roll 60 is assured. Sponge-like rubber or the like capable of flexible deformation is preferable for the material of the eccentric sleeve member 68.

Also in the case of the L size, a sleeve member of the same material may be attached to the outer circumferential face 60a of the cutter roll 60, thereby completely clearing a small gap G shown in FIG. 8B. However, the sleeve member used in this case is not a sleeve member whose center of its cross section is eccentric to the rotational center of the cutter roll 60, unlike the S size eccentric sleeve member 68; a sleeve member whose center of its cross section matches the rotational center C60 of the cutter roll 60 is used.

Other Embodiments

Above, embodiments of the invention are described. However, the invention is not limited to the embodiments, and the following variations are possible.

In the above embodiments, the welding process and the severing process are shown as an example of processing performed by the processing apparatuses 20 and 20a. However, there is no limitation to this. For example, a sawing blade may be provided instead of the flat blade 62 of the cutter roll 60 of the second embodiment, thereby forming perforation in the base material 1a.

In the above embodiments, the product size is divided into two sizes, namely, L size and S size. However, there is no limitation to this. For example, the product size may be divided into three sizes by setting a medium size, M size, between L size and S size. In such a case, the support section 34 of the sealing apparatus 20 is of course prepared to cope with the three sizes of the radius of curvature at the external contour.

In the above embodiments, the support section 34 is replaced depending on the product size. However, there is no limitation to this so long as the support position R of the base material 1a can be changed. For example, a configuration may be adopted in which a cylinder member having a piston rod that is extendable in the radial direction of the rotating body 30 with working fluid, such as a so-called hydraulic cylinder, is provided in each notched section 30c of the rotating body 30, a plate member is fixed at a tip of the piston rod, and the plate member supports the base material 1a. In such a case, for example, the plate member is positioned at the support position RL for L size in a state in which the piston rod is extended to a maximum, and the plate member is positioned at the support position RS for S size in a state in which the piston rod is retracted to a minimum.

In the above embodiments, the ultrasonic horn 50 is swayed back and forth. However, the ultrasonic horn 50 is not required to sway back and forth, that is, the ultrasonic horn 50 may be disposed above the rotating body 30 in a fixed manner.

In the above embodiments, the base material 1a is pressed against the outer circumferential face 30a of the rotating body 30 with the pressing belt device 70, so that the base material 1a is stably transported to the cutter roll 60. However, by mounting a suction device in the outer circumferential face 30a of the rotating body 30, the base material 1a may be held sucked to the outer circumferential face 30a.

In the above embodiments, the base material 1a of diaper is described as an example of continuous workpiece. However, there is no limitation to this. Continuous workpiece may be a base material for sanitation materials such as cooking sheet.

In the above second embodiments, the base material 1a is severed while held between the flat blade 62 and the blade rest member 64. However, the severing method is not limited to this. For example, shearing may be employed.

The invention claimed is:

1. A processing apparatus that performs processing on a workpiece continuous in a transport direction while transporting the workpiece in the transport direction, and performs processing on the workpiece at a predetermined processing pitch in a rotational direction of a rotating body that rotates about an axis, during movement of the workpiece in the rotational direction by the rotation of the rotating body while the workpiece is wrapped around an outer circumferential face of the rotating body, comprising:

a first processing section that is disposed at a predetermined position in the rotational direction so as to oppose the outer circumferential face of the rotating body, second processing sections that are provided at each predetermined angle in the rotational direction on the outer circumferential face of the rotating body, and that perform the processing on the workpiece in cooperation with the first processing section when a second processing section opposes the first processing section, and a support section that supports the workpiece between the second processing sections, and in which it is possible to change, depending on the processing pitch, a position at which the support section supports the workpiece.

2. A processing apparatus according to claim 1, wherein
a portion between the second processing sections on the outer circumferential face of the rotating body is notched,
a support section is disposed at the notched portion and is detachably fixed,
the support section is provided at each processing pitch, and
the support section is replaced depending on the processing pitch.

3. A processing apparatus according to claim 2, wherein
the support position of the workpiece is transferred in a radial direction of the rotating body due to replacement of the support section.

4. A processing apparatus according to any of claim 1, wherein
the workpiece is made up of a plurality of superposed sheets of a thermal welding material, and
the processing involves joining by welding the plurality of superposed sheets at the processing pitch.

5. A processing apparatus according to claim 4, wherein
the first processing section includes an ultrasonic horn that makes ultrasonic oscillation to the workpiece, and
the second processing section is an anvil including a projection section projected higher than the outer circumferential face.

6. A processing apparatus according to claim 4, wherein
a third processing section is disposed opposing the outer circumferential face of the rotating body on a downstream side of the first processing section in the rotational direction, and
when the third processing section opposes the second processing section, the third processing section works in cooperation with the second processing section and severs the workpiece at the processing pitch.

7. A processing apparatus according to claim 6, wherein
the third processing section includes a third blade member, and
the second processing section includes a fourth blade member that works in cooperation with the third blade member and severs the workpiece at the processing pitch.

8. A processing apparatus according to claim 6, wherein
between the first processing section and the third processing section, a holding device is provided that holds the workpiece so as to prevent the workpiece from separating from the outer circumferential face of the rotating body.

* * * * *